United States Patent
Oswald et al.

(10) Patent No.: US 6,923,906 B2
(45) Date of Patent: Aug. 2, 2005

(54) APPARATUS TO ESTABLISH AND OPTIMIZE SEDIMENTATION AND METHANE FERMENTATION IN PRIMARY WASTEWATER PONDS

(75) Inventors: William J. Oswald, Concord, CA (US); Franklin Bailey Green, Kensington, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 10/115,838

(22) Filed: Apr. 2, 2002

(65) Prior Publication Data

US 2002/0121477 A1 Sep. 5, 2002

Related U.S. Application Data

(62) Division of application No. 09/552,576, filed on Apr. 19, 2000, now Pat. No. 6,852,225.
(60) Provisional application No. 60/130,210, filed on Apr. 20, 1999.

(51) Int. Cl.$^7$ .................................................. C02F 3/00
(52) U.S. Cl. ....................................... 210/188; 210/220
(58) Field of Search ................................ 210/188, 220, 210/256, 262, 532.2

(56) References Cited

U.S. PATENT DOCUMENTS

| | | | |
|---|---|---|---|
| 4,005,546 A | * | 2/1977 | Oswald ........................ 47/1.4 |
| 4,162,976 A | | 7/1979 | Monson |
| 4,905,326 A | * | 3/1990 | Nakamura et al. .............. 4/488 |
| 4,997,568 A | * | 3/1991 | Vandervelde et al. ....... 210/603 |
| 6,068,773 A | * | 5/2000 | Sheaffer ...................... 210/605 |
| 6,280,636 B1 | * | 8/2001 | Locklair ...................... 210/747 |
| 6,635,177 B2 | * | 10/2003 | Oswald et al. .............. 210/602 |

OTHER PUBLICATIONS

Oswald et al., "Performance of methane fermentation pits in advanced integrated wastewater pond systems," www.cep-is.ops–oms.org/muwww/fulltext/repind54/permet/permet.html dated "Mar. 22, 1999".*

(Continued)

*Primary Examiner*—Chester T. Barry
(74) *Attorney, Agent, or Firm*—Womble Carlyle Sandridge & Rice, PLLC

(57) ABSTRACT

A method of disposing waste includes the step of forming a primary waste pond called an Advanced Facultative Pond (AFP). A stable microbiological methane fermentation zone is established within the AFP. The system constitutes a complete primary treatment of organic waste and wastewater that does not require daily sludge handling typically associated with organic waste treatment and disposal. The method of the invention converts organic compounds, including settleable solids, into methane. The invention controls sulfide odors from methane fermentation. The invention also provides a method of filtering raw wastewater through a bed of fermenting organic solids suspended by gas evolved in a fermentation zone. Hydrogen sulfide is oxidized in accordance with the invention. The technique of the invention biologically increases pH near the pond surface, thus retaining hydrogen sulfide in solution in the pond water. The biological increasing of the pH level near the pond surface increases the rate of die-away of pathogenic bacteria. The invention transforms proteins and other organic nitrogen compounds to nitrogen gas. The invention also transforms proteins and other organic nitrogen compounds to nitrogen gas; the invention detoxifies chlorinated hydrocarbons and volatile organic compounds; the invention captures and stores gases evolved from methane fermentation; the invention removes heavy metals, while establishing meromixis in fermentation cells or zones within primary wastewater ponds.

12 Claims, 6 Drawing Sheets

OTHER PUBLICATIONS

Dugan, G.L. and Oswald, William J. (1968). "Mechanisms of Anaerobic Waste Treatment." Presented at the Symposium on Potato Waste Treatment, University of Idaho, (Mar. 8, 1968), p. 15.

Green, F.B., "The Energetics of Advanced Integrated Wastewater Pond Systems," Doctoral Dissertation, University of California at Berkeley, May, 1998.

Hall, Thomas. W., Oswald, W.J., Moore, J.M., and Chen, P.H. (1981). "Recovery of Methane from Facultative Sewage Ponds," Report to the University of California Appropriate Technology Program, Project #80–89–4000, Sanitary Engineering and Environmental Health Research Laboratory, University of California, Berkeley, pp. 31.

Oswald, William J. (1960). "Stabilization and Pond Research and Installation Experiences in California," In: *Proceedings of the Symposium on Waste Stabilization Lagoons*, Kansas City, Missouri, Aug. 1–5, 1960, pp. 11.

Oswald, William J. and Golueke, C.G. (1960). "Biological Transformations of Solar Energy," In: *Advances in Applied Microbiology*, vol. 2, ed. W.W. Umbreit, Academic Press, Inc., 111 5$^{th}$ Avenue, New York, New York, pp. 42.

Oswald, William. J., Golueke, C.G., Cooper, R.C., Gee, H.K., and Bronson, J.C. (1963). "Water reclamation, algal production and methane fermentation in waste ponds," *International Journal of Air and Water Pollution*, vol. 7, pp. 627–648. Also in: *International Conference on Water Pollution Research*, London, Sep. 1962, Pergamon Press, Oxford, (1964).

Oswald, William. J. (1964). "Advances in stabilization pond design," In: *Proceeding of the Third Sanitary Engineering Conference*, Vanderbilt University, Nashville, Tennessee, May 25–26, 1964, pp. 18.

Oswald, William. J. (1964). "Feasibility of Deep Ponds for the Dan Region Project," in consultation with Tahal Water Planning for Israel Ltd., Dan Region Sewage Reclamation Project, Oct. 9, 1964, pp. 50.

Oswald, William J. (1968). "Advances in Anaerobic Pond Systems Design," In: *Advances in Water Quality Improvement*, ed. E.F. Gloyna and W.W. Eckenfelder, Jr., University of Texas Press, pp. 409–426.

Oswald, William J. and Ramani, R. (1976). "The Fate of Algae in Receiving Waters," In: *Ponds as a Wastewater Treatment Alternative*, Eds. Gloyna, E.F. et al., Water Resourse Symposium Number Nine, Center for Research in Water Resources, College of Engineering, The University of Texas at Austin, pp. 111–121.

Oswald, William J. (1983). "Municipal Sewage Waste Treatment with Microalgae," In: *Proceedings of the Regional Seminar on Microbial Conversion Systems for Food and Fodder Production and Waste Management*, Kuwait Institute for Scientific Research (KISR) and Kuwait University, Nov. 12–17, 1977, Kuwait, pp. 213–234.

Oswald, W.J. (1983). "Report On Site Visit To Ahmedabad Experimental Waste Treatment Facilities With Comments On Design Of Extended Aeration Experiments, Proposed Aerated Lagoon System, And Two Possible Alternative Ponding Systems." Report to IBRD, Dec. 1983, 6 tables, 14 figures, pp. 54.

Oswald, William J. (1985). "Advanced Algal Bacterial Systems for Liquid Waste Treatment and Disposal," In: *Proceedings of the Second National Symposium on New Proteins and Underexploited Resources*, sponsored by Instituto Nacional de Investigacao das Pescas, Lisbon, Portugal, Technical Paper read at the Second National Symposium on New Proteins and Underexploited Resources, Lisbon, Portugal, pp. 13.

Oswald, William J. (1986). "The Role of Microalgae in Liquid Waste Treatment and Reclamation," In: *Algae and Human Affairs*, C.A. Lembi and J.R. Waaland, eds., Cambridge University Press, 32 E. 57th St., New York, New York 10022.

Oswald, William J. (1987). "Preliminary Design Advanced Integrated Ponding System for Izmir, Turkey," pp. 104.

Oswald, William J. (1988). "Micro–algae and waste–water treatment" In: *Micro–algal Biotechnology*, Borowitzka and Borowitzka, (eds.), Cambridge University Press, U.K., pp. 305–328.

Oswald, William J. (1988). "Large–scale algal culture systems (engineering aspects)" In: *Micro–algal Biotechnology*, Borowitzka and Borowitzka, (eds.), Cambridge University Press, U.K., pp. 356–394.

Oswald, William J. (1994). "A Syllabus of Advanced Integrated Pond Systems," University of California at Berkeley.

Swanson Oswald Associates, Inc. (1980). "Evalutation and Report of Biomass to Energy Conversion Proposal by Livestock Systems Management," by Roy Sharp, Tulare, California. Prepared for the California Energy Commission, Dec. 1980, pp. 53.

Swanson Oswald Associates, Inc. (1985). "Wastewater Management Study—City of St. Helena," Engineering report for the City of St. Helena, California, pp. 53.

Von Hippel, David. F. and Oswald, W.J. (1985). *Collection of Methane Evolved from Waste Treatment Ponds*, UCB/SEEHRL Report 85–11, University of California, Berkeley, California, pp. 32.

Von Hippel, David F. and Oswald, W.J. (1989). "Heating Facultative Ponds To Increase Rates of Gas Evolution: A Step in the Integration of Waste–Treatment and Biomass Energy Production Using Microalgae," Report to the University of California Universitywide Energy Research Group, Sanitary Engineering and Environmental Health Research Laboratory (SEEHRL) Report No. 89–3, College of Engineering and School of Public Health, University of California, Berkeley, CA 94720, pp. 43.

U.S. Appl. No. 10/083,222, filed Oct. 24, 2001, Oswald et al.

\* cited by examiner

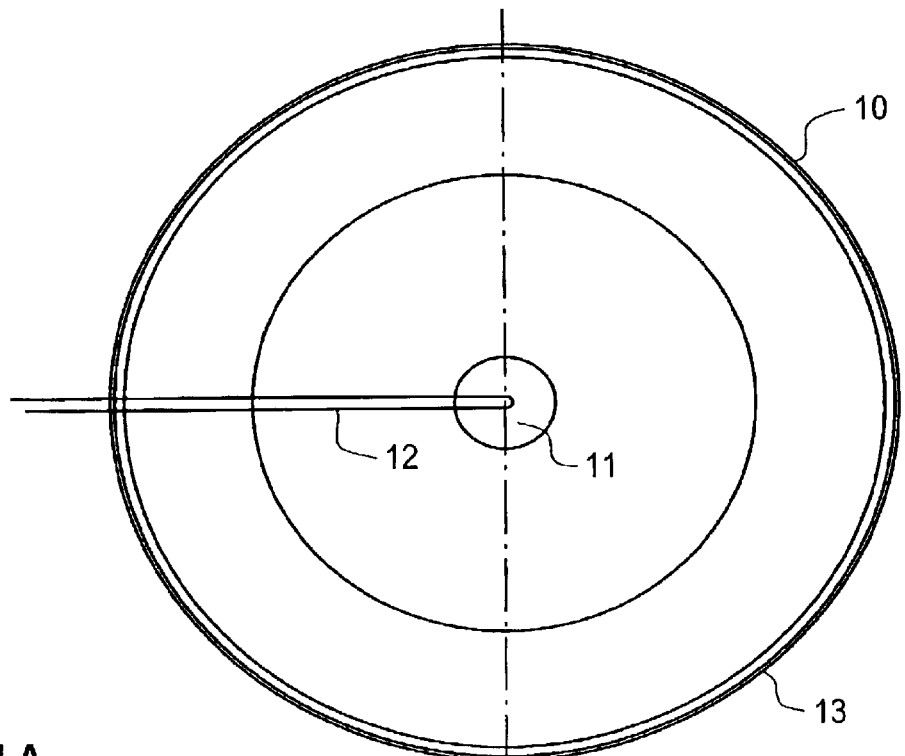
FIG. 1A PLAN VIEW
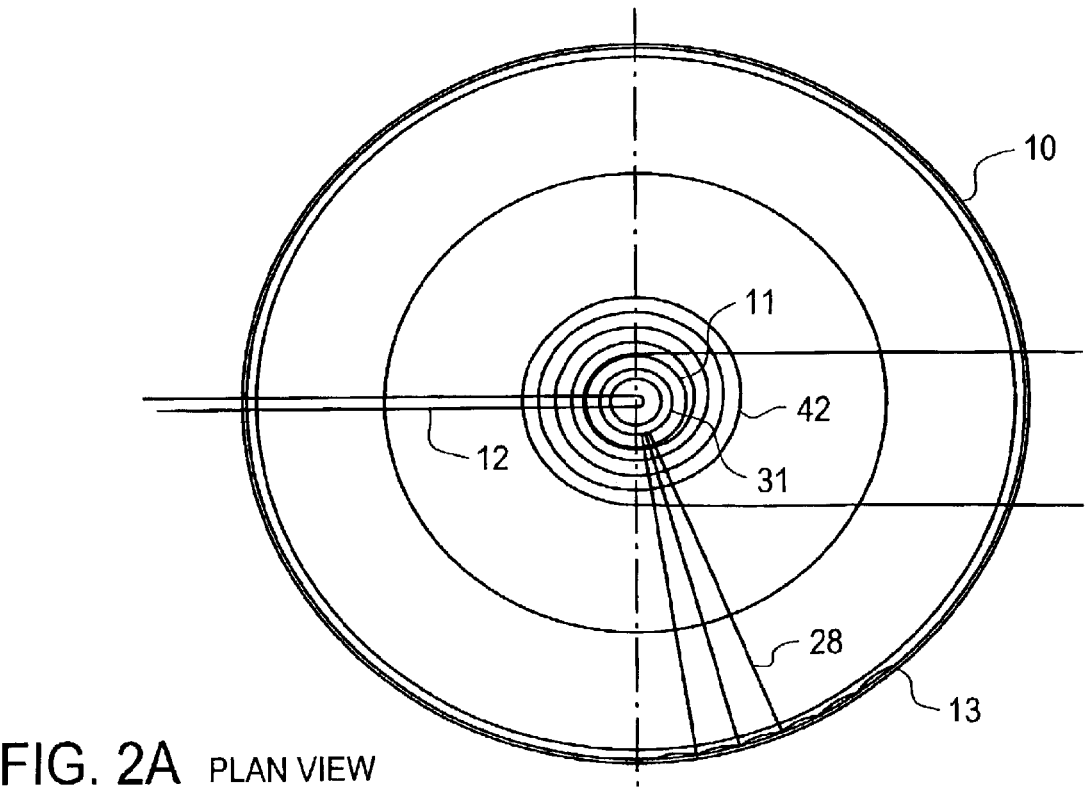
FIG. 2A PLAN VIEW

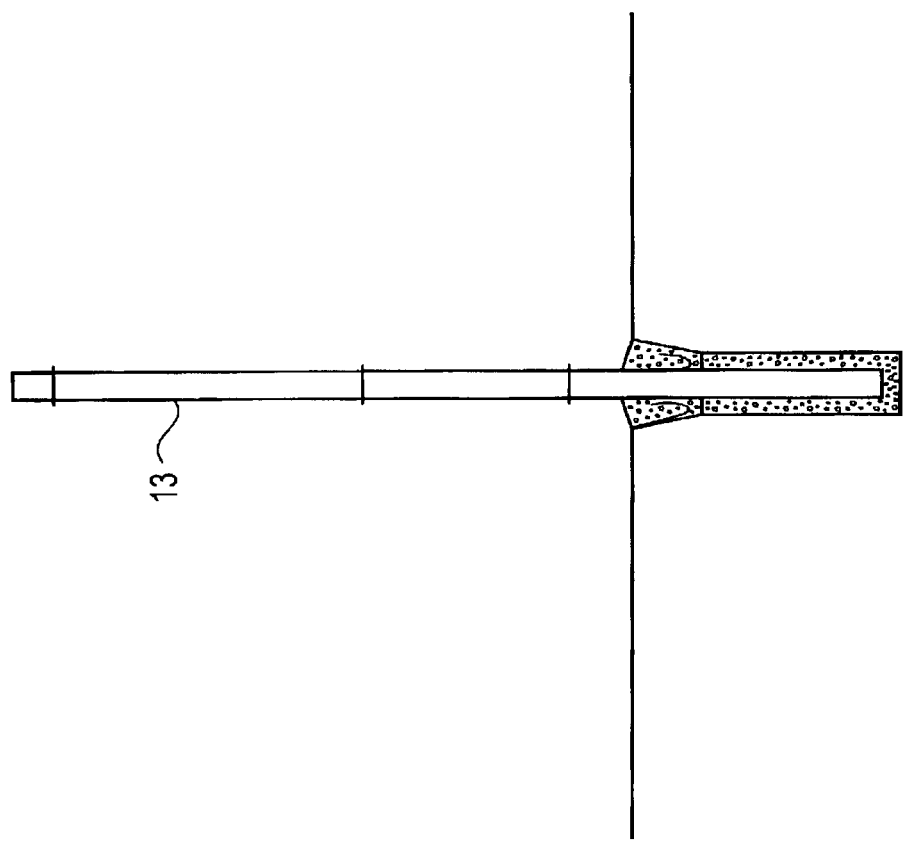

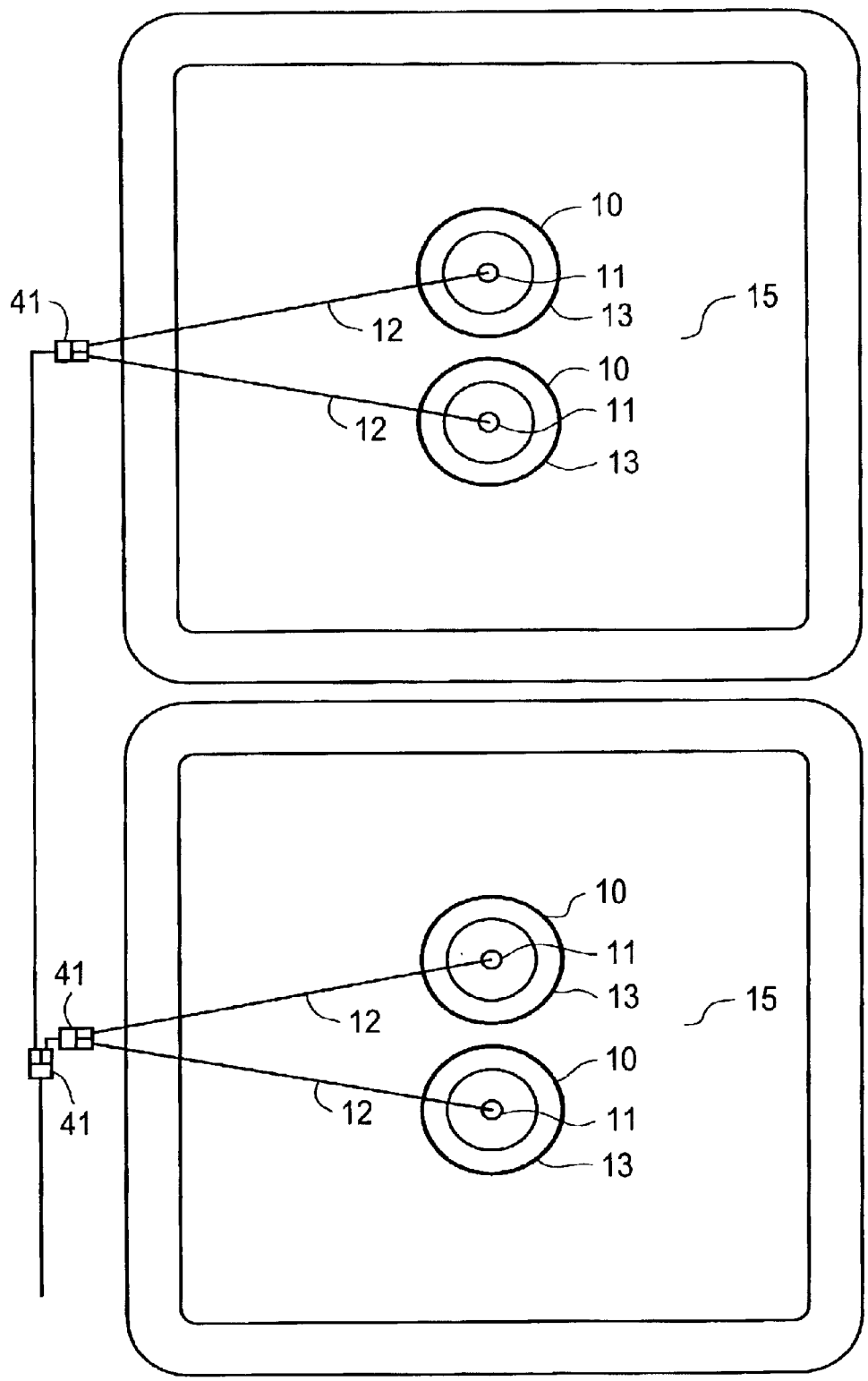
FIG. 1E  PLAN VIEW

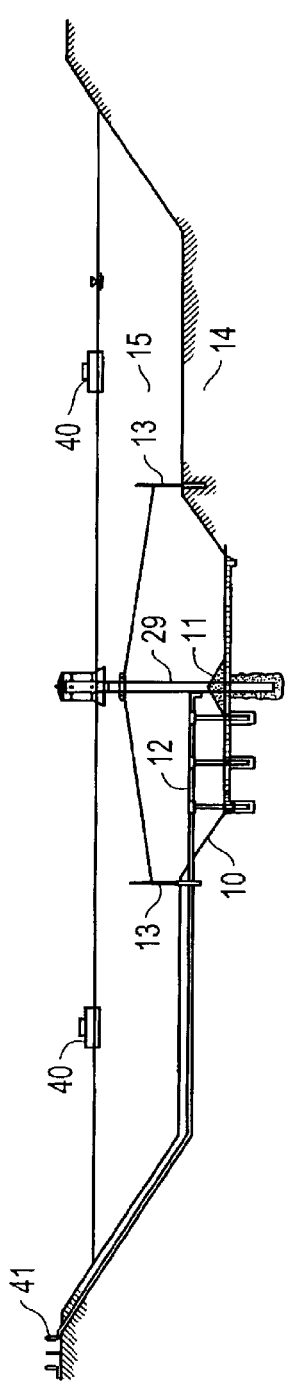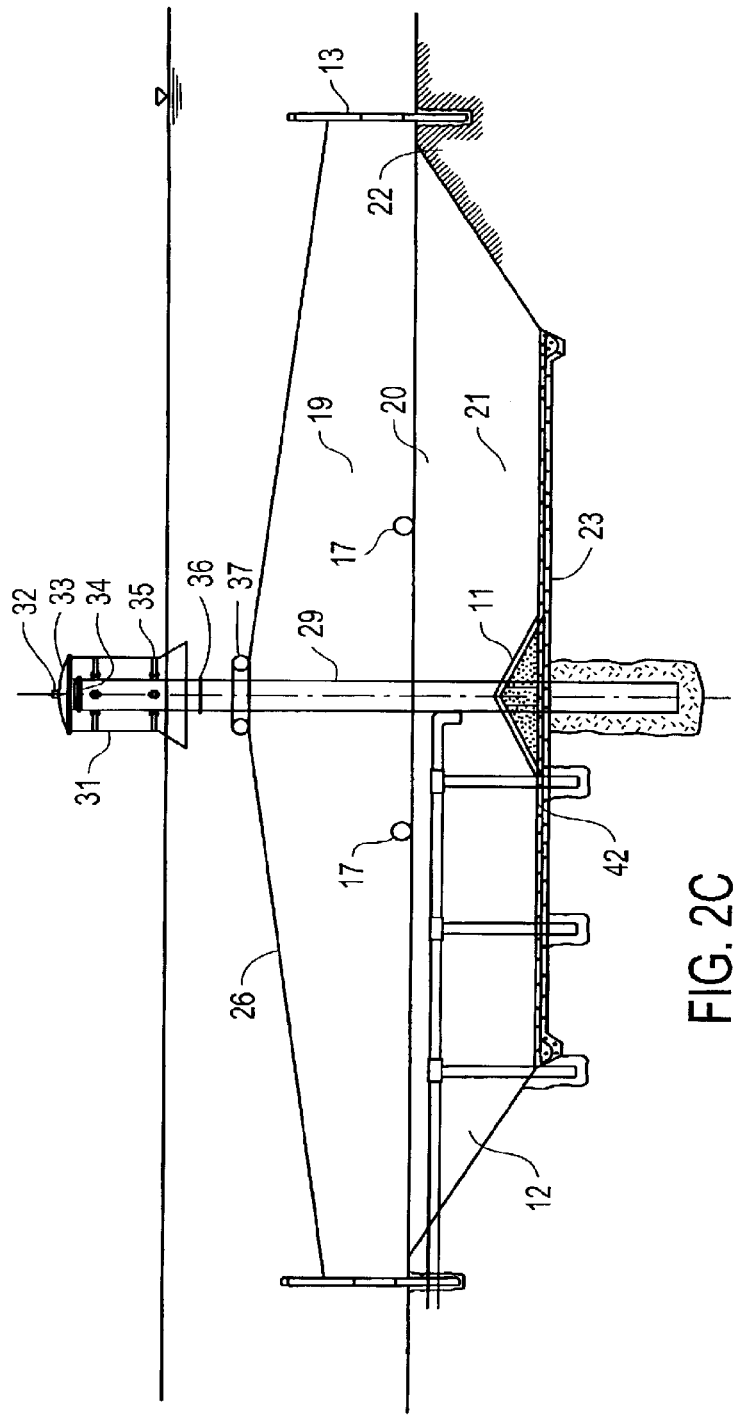

APPARATUS TO ESTABLISH AND OPTIMIZE SEDIMENTATION AND METHANE FERMENTATION IN PRIMARY WASTEWATER PONDS

This is a divisional of application Ser. No. 09/552,576, filed Apr. 19, 2000 now U.S. Pat. No. 6,852,225.

This application claims priority under 35 U.S.C. §119 (e) to U.S. provisional patent application Ser. No. 60/130,210 filed Apr. 20, 1999, which is hereby incorporated by reference in its entirety.

BRIEF DESCRIPTION OF THE INVENTION

This invention relates generally to waste treatment. More particularly, this invention relates to a new method for first stage liquid waste treatment that is simpler, safer and less costly than current methods used for primary wastewater treatment.

BACKGROUND OF THE INVENTION

The first, or primary stage of conventional liquid born waste treatment, as currently practiced, consists of sedimentation of heavy inorganic detritus called grit, followed by floatation of light materials called floatables and congealed fat called grease, and sedimentation of heavier organic solids called sludge. Grit is generally disposed of by burial on a day by day basis. Sludge is usually taken off in a side stream and treated in a separate sludge digester where its organic content is partially converted to carbon dioxide, methane, and inert gases, and the residue is de-watered and disposed of, usually by burial. Floatable material along with grease is either finely ground and introduced to a separate sludge digester with sludge or disposed of separately by burial or incineration. Under new pollution control legislation, grit, floatable materials and fresh or partially stabilized sewage sludge, unless heat treated or heavily disinfected with chlorine, are regarded as highly infectious and potentially toxic or hazardous. Thus, to handle and dispose of them safely is extremely expensive.

In view of the foregoing, it would be highly desirable to provide an improved technique for wastewater treatment. Ideally, the system would be low cost and would not require frequent waste handling.

SUMMARY OF THE INVENTION

A method of disposing waste includes the step of forming a primary waste pond. A stable microbiological methane fermentation zone is established within the primary waste pond. The system constitutes a complete primary treatment of organic waste and wastewater that does not require daily sludge handling typically associated with organic waste treatment and sludge disposal. The method of the invention converts organic compounds, including settleable solids, into methane. Carbon dioxide is also produced and used by algae. The invention controls sulfide odors from methane fermentation. The invention also provides a method of filtering raw wastewater through a bed of fermenting organic solids suspended by gas evolved in a fermentation zone. Hydrogen sulfide is oxidized in accordance with the invention. The technique of the invention biologically increases pH near the pond surface, thus retaining hydrogen sulfide in solution in the pond water. The biological increasing of the pH level near the pond surface increases the rate of die-away of pathogenic bacteria. The invention transforms proteins and other organic nitrogen compounds to nitrogen gas. The invention also detoxifies chlorinated hydrocarbons and volatile organic compounds. In various embodiments, the invention further captures and stores gases evolved from methane fermentation; and removes heavy metals, while establishing meromixis in fermentation cells or zones within primary wastewater ponds.

BRIEF DESCRIPTION OF THE DRAWINGS

For a better understanding of the invention, reference should be made to the following detailed description taken in conjunction with the accompanying drawings, in which:

FIGS. 1A–1E illustrate a waste treatment apparatus in accordance with an embodiment of the invention.

FIGS. 2A–2E illustrate a gas collection fermentation cell in accordance with an embodiment of the invention.

Like reference numerals refer to corresponding parts throughout the drawings.

DETAILED DESCRIPTION OF THE INVENTION

Figure 1B:
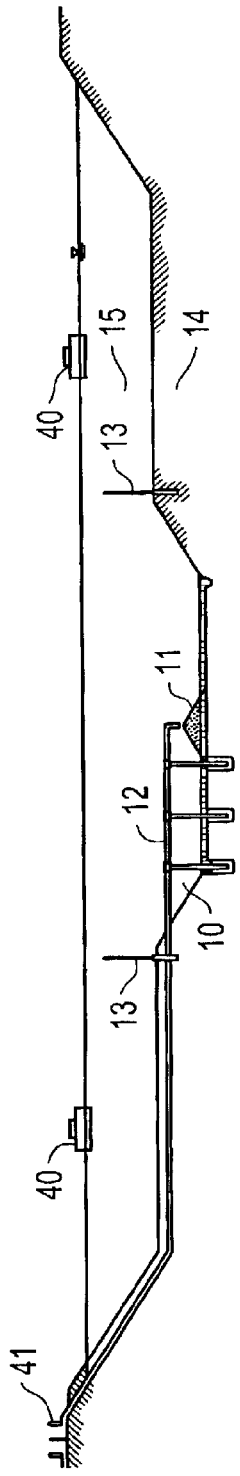

In accordance with the invention, the drudgery, hazards, and cost of day by day handling of grit, floatables, grease, and sludge are eliminated for periods of up to 20 years.

Since burial is likely to be the ultimate method for disposal of floatables, grease, grit, and sludge, the principle of this new method is to create a combined treatment and disposal site at the point of waste introduction.

In structure, this new method is carried out in two ponds—one within the other. The larger of the two surrounds and overlays the smaller pond. It is called the outer pond. The other pond is located in the bottom of the outer pond and is called the inner pond or pit. The outer pond is designed to contain aerobic or semi-aerobic wastewater. The inner pond is designed to prevent intrusion of dissolved oxygen from the outer pond and contain semi solid slurry in the highly reduced anaerobic state needed as substrate to foster methane fermentation. The inner pond is also designed to foster sedimentation of solids as well as their conversion to methane.

Because dissolved oxygen is inhibitory to methane fermentation, the fermentation zones, in one embodiment of the invention, are designed to be 1 to 10 meters deep, preferably 2 to 8 meters deep, and most preferably 3 to 5 meters deep with high walls to prevent intrusion of dissolved oxygen from the outer pond by convection or by wind driven currents. Raw, unscreened, unsettled sewage is introduced to this pit through a downdraft pipe, also called an influent pipe, its opening located near the bottom of the pit. In design, the pit volume is determined from the projected volume of inert materials such as grit, silt and sludge residue to accumulate over 20 years plus a plenum volume required for long term methane fermentation of the organic load based on projected loadings and temperatures within the pit.

The outer pond is designed to grow algae, which by their sunlight and heat absorption, create a warm surface layer of water. Algae, growing near the surface, also produce surplus oxygen, thus controlling odor, raising the pH of the water by extracting carbon dioxide, thus enhancing disinfection, and tending to precipitate metals.

To initiate the process, the pit is seeded with several tons of active moist sludge from a methane producing culture, thus assuring the presence of a large number of methane bacteria. Wastewater is then applied to the pit at a rate proportional to the organic load and temperature. One or more hydraulic equalization vents are provided to prevent washout of the pit walls and to equalize the water depth in the pit and the outer pond. The outer pond is designed to retain wastewater for 10 to 20 days depending on climate; a smaller volume is used for warmer climates and a larger volume is used for cooler climates. The overflow of the outer pond is located so that it is also 2 to 6 meters deep, and preferably 3 to 4 meters deep and extends upward 1 to 1.5 meters above the upper edge of the wall surrounding the pit. Although the overflow invert determines the depth of the outer pond, the water overflowing should be drawn from a depth of about 1.5 meters to avoid entraining floatable materials. This is done by extending the intake of the outlet pipe downward into the pond to a depth of 1.5 meters. Because materials that float are accumulated in the primary pond, their removal is provided for by installing a paved beach-like scum ramp along the edge of those portions of the pond where wind driven floating material is likely to accumulate, typically at the water's edge of the outer pond. This material, which generally consists of grease and plastic materials is quite inert, dries on the beach, and can be removed periodically by mechanical means for burial. Although it may be infectious or hazardous, very little odor or fly breeding is associated with this material due to its inert nature. Further, the fact that the scum ramp is sufficiently flat allows the floatables to dry out quickly and encourages "beaching" of the floatables by small waves.

It is important to further explain the physical, chemical and biological activity in the pits. As sewage solids enter and tend to settle, they settle through an intensely anoxic zone which contains facultative heterotrophic bacteria and methane bacteria. The interaction of these two types of bacteria is well known from experience with conventional digesters and septic tanks. Facultative organic acid forming microbes produce primarily acetate, $CO_2$, and hydrogen which are then transformed to methane by the methane bacteria. The heterotrophic and methane bacteria adhere to surfaces which are abundantly provided with the retained sewage solids. There are several unique characteristics of these pits not shared by ordinary sewage sludge digesters. First, because sewage sludge digesters are expensive, their size is such that sludge is only retained for 20 to 40 days, and therefore digestion is, at best, only partially complete, and its infectious nature only minimally eliminated. Conventional sludge digesters operate on a side stream of sludge so there is no contact between fermenting sludge and the raw waste. The pits of the instant invention are inexpensive so their residence time for the continuously fermenting and consolidating of settleable solids can be literally hundreds of days. Consequently, adaptation of microbes to unique wastes and sub optimum temperatures is possible, and fermentation of deposited organics can continue until only their inert residues remain. Such long residence time also is lethal to the ova of parasites and to other pathogens. All of the wastewater passes through and contacts this anoxic zone, before entering the outer pond. For practical purposes, all solid settleable material simply remains where deposited until decomposed to the point that only inert material remains. The volume of this inert material is remarkably small, amounting to less than 5 liters per person per year. As a result, many years are required before residual sludge removal is needed.

The gases emitted by the pits also differ significantly from that emitted by conventional digesters. Conventional digester gas usually contains about 60% methane, about 30% $CO_2$, and small amounts of $H_2S$ and the balance $N_2$, and other inert gases. The gases emitted by the anoxic pits of the invention contain about 70%–85% methane, with the balance being mostly nitrogen, and small amounts of $CO_2$, and other inert gases. The difference in gas composition is believed to result from the more complete fermentation that occurs in the pits plus the fact that overlying water in the peripheral pond absorbs most of the $CO_2$ and $H_2S$ produced in the anoxic zone. The $CO_2$ is converted to bicarbonate in the alkaline high pH surface waters and $H_2S$ is converted to the HS-ion and eventually to sulfate as it emerges toward the outer pond surface. The outer pond near its surface is highly aerobic—its free molecular oxygen content either resulting from the growth of microalgae in the layer of water above the pit walls or from re-circulation of oxic waters from a high rate pond in series with the pond being disclosed, or in rare cases, when needed, by supplementary mechanical aeration.

Functionally, the pits are highly anoxic and strongly reducing. Carbohydrates are quickly converted to methane. Proteins and amino acid are hydrolyzed by proteolytic enzymes, and ammonium is released to be converted to nitrate and $N_2$ gas via heterotrophic nitrification and de-nitrification. Lipids are converted to glycerides and then to methane. Some toxic substance such as certain chlorinated hydrocarbons are dissociated and destroyed. Heavy metals such as lead, chromium, and others combine with sulfides in the fermentation zone and are retained as precipitates along with other inert residuals.

Organic and inorganic sludges with adhering gas tend to be lifted by gas buoyancy, but as the mixture rises toward the level of the top of the pit walls, the adhering gas bubbles expand in size and break away from the sludge and rise alone to the surface. The sludge resettles passing downward through any new sewage entering the system. This continuously working sludge-bed has a filtering effect on new particles and dissolved organics entering the system tending to carry them downward and to retain them within the sludge blanket. Microbes adhering to the settleable solids adsorb soluble organics as well as colloidal particulates, thus reducing soluble and colloidal biochemical oxygen demand (BOD). Also, since the column of water above the pit bottom is 6–8 meters (18–25 feet), a pressure of 500–600 grams/cm$^2$ (slightly over 7 psi) compresses loose solids tending to increase their density and hence their rate of sedimentation. Accordingly, many substances which would float if deposited at the surface do not float when injected into the sludge blanket. Individual pits should ideally be 0.09 hectare and not be larger than about 0.1 hectare (¼ acre) so when larger areas are needed to maintain load criterion, several pits should be used. A cone, or flow deflector, is used to assure distribution of sludge over the pit bottom area. Because it may be necessary to de-water and clean pits after 20 years, more than one pond pit system in parallel should be used. When greater than one pond pit system is used, the ponds should be fed by way of a hydraulic head equalizing distributor 41 on the influent pipe 12. Moreover, equilateral bifucation of the influent pipe 12 via the hydraulic head equalizing distributor permits equal loading of up to four pits within one outer pond 15. In large systems, several pits or fermentation cells would be aligned in multiple parallel fermentation trenches running transfer to the prevailing wind. In this configuration, each individual pit would be separated by a baffle so that its surface area would be no greater than about 0.1 hectare.

The general nature of the invention has now been described. Attention now turns to a more detailed discussion of different embodiments of the invention. The key to successful methane fermentation is the establishment of protected anoxic zones where naturally present heterotrophic and methane bacteria flourish, within primary waste ponds, sometimes referred to as Advanced Facultative Ponds (AFP). The zones are created by preventing the intrusion of cold water containing dissolved oxygen. This protection can be achieved economically by isolating the fermentation zone with a surrounding wall or other vertical structure to prevent the intrusion of cold, oxygen-bearing water. Crucial factors for the special zones of stable methane fermentation are: depth, surface area, volume, the type and location of the inlet structures, the height of the current deflector or surrounding wall, the location of special vents, hydraulic and organic loading rates, the exclusion of storm water and inert solids or grit, and the residence time of the settled solids. The advantages of in-pond methane fermentation include the elimination of the need to remove, handle, and dispose of sludge residuals over long periods of time, usually several decades; the purification and enrichment of methane gas emerging from the zones of fermentation; the reduction, precipitation, and removal of heavy metals; the immobilization of parasites; the bio-degradation of many toxic organic compounds; and, significant removal (60% or more) of BOD.

Figure 1C:
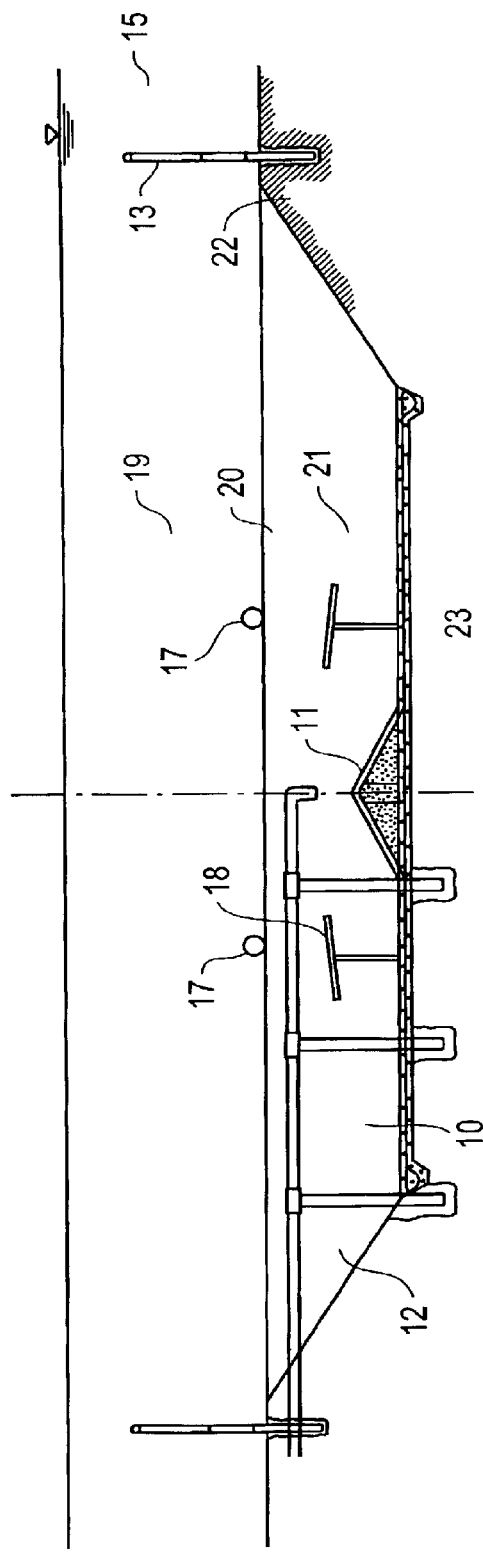

FIGS. 1A–1E illustrate the system of the invention. FIG. 1A is a top view of the inner pond or pit 10. The inner pond 10 generally includes a flow deflector 11, an influent pipe 12 and an oxygen deflector 13. The oxygen deflector should be on the entire periphery of the inner pond 10. FIG. 1B represents a cross-sectional view of the Advanced Facultative Pond 14, which comprises both the inner pond 10 and the outer pond 15. The outer pond 15 may be any shape, but typically is either round or rectangular. Also shown within FIG. 1B are the flow deflector 11 and the influent pipe 12. Although a single inner pond 10 is shown, it is to be understood that there may be more than one inner pond 10 in each advanced facultative pond 14. All inner ponds 10, however, must be located away from any floating or surface aerators 40. As previously noted, supplemental mechanical aeration is sometimes needed when, due to light or temperature inhibition, there is insufficient photosynthesis to control odors. Aerators 40 must be located outside and at least 10 meters from the outside edge of the fermentation pits. In a preferred embodiment, floating surface aerators of the injection type are used since they create no aerosols and are very quiet. Their flow direction, however, must be away from the fermentation pits. The number and size of the aerators is determined by the organic load coming from the fermentation pits. Moreover, the location of the inner pond 10 may be varied within the Advanced Facultative Pond 14. FIG. 1B further shows a special influent structure 41 designed to permit only design flow or less to enter the fermentation zones. FIG. 1C represents a more detailed description of the inner pond 10 within the Advanced Facultative Pond 14. Specifically depicted are the flow deflector 11, the influent pipe 12, the oxygen deflector 13, the hydraulic pressure equalization vents 17, also called an overflow pipe, the deflector membrane 18, the buffer zone 19, the settling zone 20, the fermentation zone 21, the high density polyethylene (HDPE) lined walls 22, which forms a strong, thick plastic sheeting used to line ponds to keep them from leaking outward, the slope of which will depend upon local soil conditions, and a concrete floor reinforced with No. 6 reinforcing bars 23, which can be made of any non-corrosive material, including, but not limited to stainless steel and fiberglass. Storm flows, which usually contain dissolved oxygen, are directed to the outer pond 15 by a special bypass in the head works within the influent pipe 12. In a preferred embodiment, the hydraulic pressure equalization vent 17 is at a right angle to the prevailing winds to avoid wind induced pressure differentials from causing back flow of oxygenated water that could impair fermentation. For the particles and gases moving through the buffer zone 19, the settling zone 20 and the fermentation zone 21, in an embodiment of the invention, the maximum upflow velocity should be 1.8 meters per day. The buffer zone 19 represents the top layer of the fermentation pit where gases are rapidly traveling to the surface. The settling zone 20 represents where solid particles that were traveling upward with the gases are released from the gases and held back by frictional drag and eventually re-settle in the fermentation zone 21. The fermentation zone 21 is where the facultative and methane bacteria exist. FIG. 1D represents a detailed depiction of the oxygen deflector 13. In a preferred embodiment, the diameter of the inner pond 10, which is surrounded by the oxygen deflector 13 should not be greater than 33 square meters in order to maintain the upper aperture area of less than 0.1 hectare. Larger areas would be prone to mixing during strong winds. The oxygen deflector 13 is composed of heavy wall, polyvinyl chloride (PVC) posts, or similar material. Overall, the oxygen deflector 13 should be about 3 to 6 meters in length and preferably 4 to 5 meters in length with about 2.5 meters being above-grade (above the water level). In a specific embodiment, HDPE should be woven around and fastened to the oxygen deflector 13. FIG. 1E represents the system when inner and outer ponds are placed in parralel.

Figure 2D:
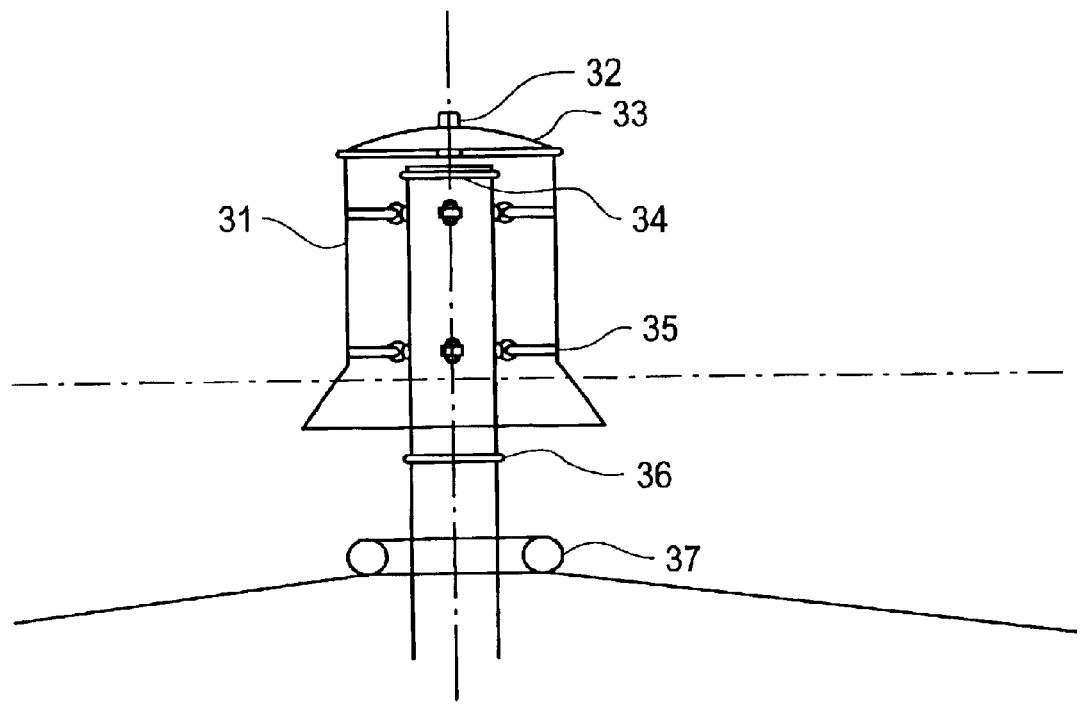
Figure 2E:
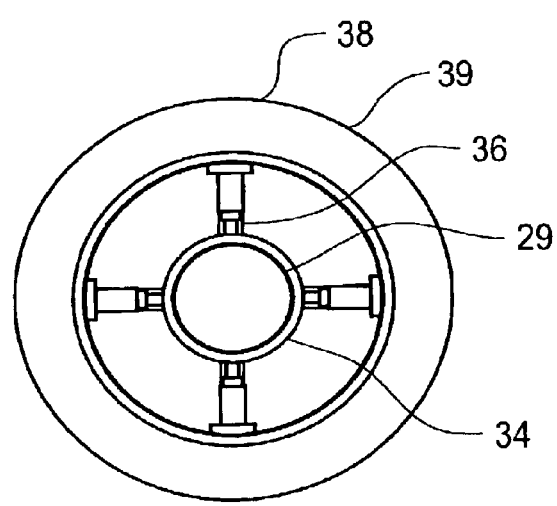

FIGS. 2A–2E illustrate a gas collection fermentation system of the invention. FIG. 2A represents a top view of the inner pond 10. Inner pond 10 generally includes a flow deflector 11, an influent pipe 12, an oxygen deflector 13, a gas deflector canopy 28, also known as a submerged gas collector, a gas fueled heat power generator 42 and a a gas cap 31. In a preferred embodiment of the invention, the gas deflector canopy 28 is composed of a reinforced plastic membrane. The uplift of gas pressure under the canopy requires that the canopy material must be reinforced with strips of webbing to keep it from tearing. These strips extend from the periphery of the oxygen deflector 16 to the canopy vertical positioning float 37. The oxygen deflector should be on the entire periphery of the inner pond 10. FIG. 2B, similar to FIG. 1B, represents a cross-sectional view of the Advanced Facultative Pond 14, which comprises both the inner pond 10 and the outer pond 15. Also shown within FIG. 2B are the flow deflector 11, the influent pipe 12 and a central mast pipe 29 used for gas transport. In a preferred embodiment, the pipe is made of stainless steel. As with FIG. 1B, although a single inner pond 10 is shown, it is to be understood that there may be more than one inner pond 10 in each advanced facultative pond 14. All inner ponds 10, however, must be located away from any aerators. Moreover, the location of the inner pond 10 may be varied within the Advanced Facultative Pond 14. FIG. 2C represents a more detailed description of the inner pond 10 within the Advanced Facultative Pond 14. Specifically depicted are the flow deflector 11, the influent pipe 12, the oxygen deflector 13, the hydraulic pressure equalization vent 17, the deflector membrane 18, the buffer zone 19, the settling zone 20, the fermentation zone 21, the HDPE lined walls 22, the slope of which will depend upon local soil conditions, No. 6 Rebar 23, a gas deflector canopy 28, a central mast pipe 29, a heavy wall containing a heating coil or fuel cell 30 and a gas cap 31. In a preferred embodiment, the heating coil within the heavy wall 30 is 2.5 cm in diameter. FIG. 2D represents a detailed depiction of the gas cap 31. Specifically, the gas cap 31 comprises a gas outlet 32, a flange cap 33, a top stop ring 34, a bottom stop ring 35, a cap roller 36 and a canopy vertical positioning float 37, also known as a buoyancy ring. The flange cap 33 is gas tight and is sealed after the top stop ring 34 is in place. Moreover, the top stop ring 34 is put in place after the flange cap 33 is in place. FIG. 2E depicts a top view of the gas cap 31. Specifically depicted are a gas cap lower skirt 38, a gas cap main body 39, a cap roller 36, a central mast pipe 29 and a top stop ring 34. The gas produced from the fermentation pits travels along the central mast pipe and is collected in the gas cap. The collected gas can then be passed through the gas outlet 32 to, for example, a power generator for the production of electricity.

The first reactors in the system of the invention are the specially designed fermentation zones within two or more Advanced Facultative Ponds (AFP). The purpose of the fermentation zones is to permit complete sedimentation of the settleable suspended solids and their microbiological conversion by naturally-occurring heterotrophic and methane-forming bacteria to water, methane, carbon dioxide, and nitrogen gas. Further purposes are sedimentation and retention of parasite ova, precipitation of heavy metals, and the biodegradation of toxic organic chemicals. In a preferred embodiment, fermentation zones should be 6 to 8 or more meters in depth below the AFP/water surface with a top surface area of not more than 0.09 hectare (900 square meters). The influent wastewater rises at a velocity in the range of 0.7 and 1.4 mm per minute. The redox potential must be in the range of −0.3 to −0.5 volts, and the pH should be in the range of 6.5 to 7.5. The 0.09-hectare aperture is necessary to reduce the probability that wind-induced convective currents will intrude bringing dissolved oxygen, higher pH, and positive redox potential water into the fermentation zone.

The methane forming microbes are extremely sensitive to, and are inactivated by, pH levels above 7.5 and below 6.5. If any water with adverse chemical characteristics enters the fermentation zone, the methane-forming bacteria may be inactivated and take weeks to resume their normal metabolic activity. The low overflow and consequently low hydraulic loading rates in the fermentation zones are designed to permit near complete bioconversion of volatile organic solids to gaseous and liquid products. The very low overflow velocity also increases the probability of pathogenic parasite ova retention.

In operation, after grit removal as needed, and comminution or grinding, the otherwise untreated wastewater is introduced into the fermentation pit of the AFPs. Systems, which often having intermittent pumped influent, may require carefully staged pump selection, or a surge chamber to avoid the washout of essential bacteria and settleable solids. High storm flows in combined sewers and excessive sewer infiltration and inflow require a special influent structure 41 designed to permit only the design flow or less to enter the fermentation zones. Higher than design flows, usually resulting from storm runoff and related infiltration and inflow, should be automatically bypassed into the AFPs, thus protecting the special environment within the fermentation zone from dissolved oxygen (DO) in the influent and from excess upflow velocity and consequent wash out. The use of such a bypass in the fermentation zone influent system is an important innovation in pond design, although it makes use of a well-known hydraulic device; a lateral overflow structure that diverts high flows from the pit to the outer pond. Influent flow dividers must be designed to avoid aeration and entrainment of air due to turbulence. Design or lesser flows are conveyed by pipe 12 into the center of the fermentation zones and released vertically downward approximately 1.0 meter above the tip of the flow deflector. Because of the low upflow velocity (<1.8 meter per day) and the compression of solids by hydrostatic pressure increasing their density, settleable primary solids tend to remain near the bottom of the fermentation zone creating a circular fall-out mound around and near the flow deflector. As this mound builds up in depth, its base becomes extremely anoxic permitting anaerobiosis culminating in robust methane fermentation. Studies of gas emission from these zones indicate that up to 90% of the gas produced is evolved within five meters of the inlet. Bubbles of $CO_2$, $N_2$ and $CH_4$ form, adhere to, and lift the solid particles. Bubble expansion soon causes the solids to separate and re-settle while the gas rises to the surface. Separation of gas bubbles and solid particles occurs because the gas bubbles expand and accelerate as they rise, whereas the solid particles are held back by frictional drag and eventually drop off and resettle as the enlarging and accelerating bubbles rise toward the surface.

These biological, chemical, and physical interactions result in an anaerobic field of rising and falling particles through which all of the influent wastewater must pass and by which it is coarsely filtered. This method to improve in-pond methane fermentation is totally different from conventional sewage treatment in which the settleable solids or primary sludge are separated from the influent wastewater and conveyed into separate sludge digesters for anaerobic digestion. Because of the high cost of separate sludge digesters, the size and volume of separate sludge digesters are based on a sludge residence time required to produce drainable sludge, e.g. 40 days, rather than the time required for complete methane fermentation. Because the fermentation zones in AFPs may be constructed of earthwork and plastic, they are sufficiently inexpensive that they can be made large enough to permit almost infinite retention and very complete methane fermentation of the settleable volatile solids and to eliminate the need for the disposal of organic sludge over several decades.

Compared with conventional treatment steps of sedimentation, separate sludge digestion, and aerobic oxidation, the advantages of in-pond sedimentation and fermentation of settleable solids are: the yield of bacterial cell material is much lower; solids concentration is not limited by oxygen transfer; there is minimal need to provide aeration; supplementary nutrients are not usually required; and, rather than consuming energy for mechanical aeration, heat power or fuel cell energy production from the recovery of methane gas may be simply attained by methane capture using the apparatus shown in FIGS. 2A–2E.

Beyond the flow deflector, the fermentation zone bottom is designed flat and lined with concrete sufficiently strong to support wheeled equipment should cleaning ever be needed. If gas collection and power generation with the collected gas are intended, in one embodiment of the invention, the central part of the methane fermentation zone should be designed to contain embedded heavy wall stainless steel pipes that are connected to a closed heat exchange system on the gas fueled heat power generator 42. Gas engine heat recovery provides small amounts of incremental heat to accelerate and improve the efficiency of methane fermentation in the concentrated bottom sludges of the fermentation zone. Once established, the media in the fermentation zone becomes more concentrated, and hence sufficiently more dense than the overlying water that the overlying water will not displace it even though the media is warmer than the overlying water, a condition called meromixis. The special media and environment within the fermentation zone is laterally isolated from waters of the surrounding AFP; for example, by means of vertical walls, most economically made from plastic sheeting supported by concrete embedded posts made of plastic, wood, or composite material.

If gas capture is not intended, the top of the walls should be about one and one third meters below the fixed water surface of the overlying AFP. This provides for an approximately one meter thick strata at the surface of the AFP which usually contains sufficient dissolved oxygen to act as a buffer against the release of objectionable odors that may otherwise be present in the gases entering the atmosphere above the fermentation pit.

If gas capture and power generation are intended and included in the design, as may eventually be required in order to control the emission of methane, a potent greenhouse gas, the top of the oxygen deflector should be 1.5 to 2.5 meters below the fixed water surface of the AFP to permit gas collection using a submerged focusing gas collector and surface gas cap (see FIG. 2B). The 1.5 to 2.5 meter edge submergence permits the submerged gas collector 28 to be sloped upward by the buoyant ring 37 so that gas intercepted by the submerged gas collector will migrate diagonally upward to a central surface gas cap positioned directly above the fermentation zone. In a separate embodiment, the central mast pipe may be hollow for gas storage. The submerged gas collector (deflector) and surface gas cap are held in a central location by a rigid mast of plastic, wood or other non-toxic material. Concerning other design details, the oxygen deflector should be between 1.5 and 2.5 meters below the fixed water surface in the AFP to provide a photosynthetically or mechanically induced dissolved oxygen containing buffer strata that removes objectionable odors.

Although FIG. 1 and FIG. 2 depict a circular fermentation zone, other configurations that preserve design criteria of depth, aperture or surface area, volume, and loading rates may be used. If rectangular fermentation zones are needed to meet other design criteria, their length should be at right angles to the prevailing wind direction, and they should be divided into individual cells which conform to the areal design criteria of 0.09 hectare.

The foregoing description, for purposes of explanation, used specific nomenclature to provide a thorough understanding of the invention. However, it will be apparent to one skilled in the art that the specific details are not required in order to practice the invention. In other instances, well known circuits and devices are shown in block diagram form in order to avoid unnecessary distraction from the underlying invention. Thus, the foregoing descriptions of specific embodiments of the present invention are presented for purposes of illustration and description. They are not intended to be exhaustive or to limit the invention to the precise forms disclosed, obviously many modifications and variations are possible in view of the above teachings. The embodiments were chosen and described in order to best explain the principles of the invention and its practical applications, to thereby enable others skilled in the art to best utilize the invention and various embodiments with various modifications as are suited to the particular use contemplated. It is intended that the scope of the invention be defined by the following claims and their equivalents.

What is claimed is:

1. A liquid waste disposal apparatus, comprising:
   an outer pond having an open surface and comprising aerobic wastewater, and;
   at least one inner pond disposed within and below said outer pond, wherein at least one or said at least one inner pond comprises a bottom that is at least 6 meters below said open surface and comprises semi-solid anaerobic slurry to allow methane fermentation to occur; and
   an influent pipe configured to pass liquid waste to said at least one inner pond.

2. The apparatus of claim 1, further comprising a flow deflector positioned below an exit opening of said influent pipe.

3. The apparatus of claim 1, further comprising an oxygen deflector disposed within said outer pond and configured to reduce the flow of dissolved oxygen from said outer pond into said at least one inner pond.

4. The apparatus of claim 1, further comprising an oxygen deflector that comprises a wall that surrounds a periphery of said at least one inner pond.

5. The apparatus of claim 1, further comprising an aerator in said outer pond.

6. The apparatus of claim 1, wherein said at least one inner pond has a top surface area of less than approximately 0.09 hectare.

7. The apparatus of claim 1, wherein said at least one inner pond has a depth of approximately 6 to 8 meters.

8. The apparatus of claim 1, wherein said outer pond has a depth of approximately 4 to 6 meters.

9. The apparatus of claim 1, further comprising a gas collection system configured to collect gas produced by a methane fermentation zone within said at least one inner pond.

10. The apparatus of claim 9, wherein said gas collection system comprises:
    gas deflector canopy disposed near a top portion of said at least one inner pond and below said open surface and having an apex;
    a central mast pipe positioned vertically in said at least one inner pond having a bottom end disposed within a bottom of said at least one inner pond and a top end above said open surface and passing through said apex of said gas deflector; and
    a gas cap disposed on said top end of said central mast pipe.

11. A liquid waste disposal apparatus, comprising:
    an outer pond having an open surface and configured to hold aerobic wastewater; and;
    at least one inner pond disposed within and below said outer pond, wherein at least one of said at least one inner pond comprises a bottom that is at least 6 meters below said open surface and is configured to hold semi-solid anaerobic slurry to allow methane fermentation to occur;
    an influent pipe configured to pass liquid waste to said at least one inner pond; and
    a flow deflector positioned below an exit opening of said influent pipe.

12. A liquid waste disposal apparatus, comprising:
    an outer pond having an open surface and configured to hold aerobic wastewater; and;
    at least one inner pond disposed within and below said outer pond, wherein at least one of said at least one inner pond comprises a bottom that is at least 6 meters below said open surface and is configured to hold semi-solid anaerobic slurry to allow methane fermentation to occur;
    an influent pipe configured to pass liquid waste to said at least one inner pond; and
    an oxygen deflector disposed within said outer pond and configured to reduce the flow of dissolved oxygen from said outer pond into said at least one inner pond.

* * * * *